United States Patent
Sen

(10) Patent No.: US 6,366,086 B1
(45) Date of Patent: Apr. 2, 2002

(54) APPARATUS AND METHOD FOR MAGNETIC RESONANCE LOGGING

(75) Inventor: Pabitra N. Sen, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 09/199,019

(22) Filed: Nov. 24, 1998

Related U.S. Application Data

(63) Continuation-in-part of application No. 08/936,892, filed on Sep. 25, 1997, now Pat. No. 6,166,543.

(51) Int. Cl.$^7$ ................................................ G01U 3/00
(52) U.S. Cl. ..................................................... 324/303
(58) Field of Search ................................ 324/303, 300, 324/314, 318, 322

(56) References Cited

U.S. PATENT DOCUMENTS

| | | | |
|---|---|---|---|
| 3,439,260 A | * | 4/1969 | Bene ........................... 324/303 |
| 3,667,035 A | * | 5/1972 | Slichter ....................... 324/303 |
| 4,035,718 A | | 7/1977 | Chandler |
| 4,528,508 A | | 7/1985 | Vail, III |
| 4,656,422 A | | 4/1987 | Vail, III et al. |
| 4,710,713 A | | 12/1987 | Strikman ..................... 324/303 |
| 4,717,878 A | | 1/1988 | Taicher et al. |
| 4,724,385 A | | 2/1988 | Vail, III |
| 4,804,918 A | | 2/1989 | Vail, III |
| 5,055,787 A | | 10/1991 | Kleinberg et al. |
| 5,055,788 A | | 10/1991 | Kleinberg et al. .......... 324/303 |
| 5,363,041 A | | 11/1994 | Sezginer |
| 5,428,291 A | | 6/1995 | Thomann et al. |
| 5,596,274 A | | 1/1997 | Sezginer |
| 6,177,794 B1 | * | 1/2001 | Stoeffl ........................ 324/303 |

FOREIGN PATENT DOCUMENTS

| | | |
|---|---|---|
| WO | PCT/EP96/0291 | 6/1996 |
| WO | PCT/US96/15301 | 9/1996 |

OTHER PUBLICATIONS

S. Connolly, G. Glover, D. Nishimura, and A. Macovski, MRM 18, 28, 1991.
Webb, Rev. Sci. Inst., V48, p. 1585, 1978.
Ernst et al., "Principles Of Nuclear Magnetic Resonance In One And Two Dimensions", pp. 91–241, Clarendon Press, 1987.
S.C. Bushong, ScD, "Magnetic Resonance Imaging Physical and Biological Principles", Houston, Texas, pp. 279–297.
Bagguley, D.M.S., "Pulsed Magnetic Resonance: NMR, ESR, And Optics A Recognition Of E.L. Hahn", 1992, pp. 317–345.
Melton and Pollak, JMRA 122, pp. 42–49, 1996.
Solomon, Phys. Rev. Lett. 2, pp. 301–302, 1952.

(List continued on next page.)

Primary Examiner—Louis Arana
(74) Attorney, Agent, or Firm—William B. Batzer; Martin M. Novack

(57) ABSTRACT

A method for the determining a nuclear magnetic resonance characteristic of earth formations surrounding a borehole, includes the following steps: providing a logging device that is movable through the borehole, the logging device having a longitudinal axis; providing a first coil in the logging device, for generating a magnetic field in the formations; providing a second coil in the logging device; applying a polarizing signal to the first coil; detecting, with the second coil, magnetic resonance of spins in the formations that are precessing around earth's magnetic field; and providing a third coil in the logging device, the third coil being operative to produce a further magnetic field in the borehole that reduces the contribution of spins in the borehole to the magnetic resonance detected by the second coil.

24 Claims, 6 Drawing Sheets

OTHER PUBLICATIONS

E.J. Wells And K. H. Abramson, JMR, 1, pp. 378–392, 1969.

Hwang, VanZijil and Garwood, JMR, 133, pp. 200–203, 1998.

Garwood and Ugurbill, "$B_1$ Insensitive Adiabatic RF Pulses" in "Basic Principles and Progress", M. Ruin and J. Seelig, Eds., pp. 109–144, Springer–Verlag, N.Y., 1992.

A. Tannus and M. Garwood, JMR A 120, pp. 133–137, 1996.

E. Kupce and R. Freeman JMR A 118, pp. 299–303, 1996.

T.L. Hwang and A.J. Shaka, JMR A 112, pp. 275–279, 1995.

M.H. Levitt and R. Freeman JMR 43, pp. 65–80, 1981.

V. Ermakov, J. Bohlen, G. Bodenhausen, JMR A 103, pp. 226–229 1993.

O.A. Trushkin, O.A. Shushnakov, & A.V. Legchenko, "Surface NMR Applied to an Electronconductive Medium", Geophysical Prospecting, 1995, 43, 623–633.

O.A. Shushnakov, "Surface NMR Measurement of Proton Relaxation Times in Medium to Coarse–Grained Sand Aquifier", 1996, Magnetic Resonance Imaging, vol. 14, Nos. 7/8 pp. 959–960.

R.C. Merrick, S.H. Coutruie, & D.L. Best, "An Improved Nuclear Magnetism Logging System and Its Application to Formation Evaluation", Sep. 23–26, 1979, Las Vagas, Nevada, SPE8361.

S. Connolly, D. Nishimura, A. Macovski JMR 83, pp. 324–334, 1989.

M. Garwood and Y. Ke, J, Mag. Res., 94, pp. 511–525, 1991.

T. Hwang, P. Van Zijl and M. Garwood, JMR 124, pp. 250–254, 1997.

R. de Graaf, K. Nicolay, M. Garwood, MRM, 35, pp. 652–657, 1996.

A. Abragam, The Principles Of Nuclear Magnetism, Oxford Univ. Press, 1961 pp. 65–68, 86, Fig. III 5 and III 6.

P. Mansfield, Pulsed Magnetic Resonance, pp. 317–345, 1992.

* cited by examiner

US 6,366,086 B1

APPARATUS AND METHOD FOR MAGNETIC RESONANCE LOGGING

RELATED APPLICATIONS

This is a continuation-in-part of U.S. patent application Ser. No. 08/936,892, filed Sep. 25, 1997, now U.S. Pat. No. 6,166,543, and assigned to the same assignee as the present Application. The subject matter of present Application is related generally to the subject matter of U.S. patent application Ser. No. 09/198,715, now U.S. Pat. No. 6,107,979, and the subject matter of U.S. patent application Ser. No. 09/198,535, now U.S. Pat. No. 6,133,735, both filed of even date herewith, and both assigned to the same assignee as the present Application.

FIELD OF THE INVENTION

This invention relates to nuclear magnetic resonance logging, and, more particularly, to a method and apparatus for magnetic resonance logging of an earth borehole to obtain information about properties of formations surrounding the earth borehole.

BACKGROUND OF THE INVENTION

General background of nuclear magnetic resonance (NMR) well logging is set forth, for example, in U.S. Pat. No. 5,023,551. Briefly, in NMR operation the spins of nuclei align themselves along an externally applied static magnetic field. This equilibrium situation can be disturbed by a pulse of an oscillating magnetic field (e.g. an RF pulse), which tips the spins away from the static field direction. After tipping, two things occur simultaneously. First, the spins precess around the static field at the Larmor frequency, given by $\omega_0 = \gamma B_0$, where $B_0$ is the strength of the static field and $\gamma$ is the gyromagnetic ratio. Second, the spins return to the equilibrium direction according to a decay time T1, the spin lattice relaxation time. For hydrogen nuclei, $\gamma/2\pi = 4258$ Hz/Gauss, so, for example, for a static field of 235 Gauss, the frequency of precession would be 1 MHz. Also associated with the spin of molecular nuclei is a second relaxation, T2, called the spin-spin relaxation time. At the end of a ninety degree tipping pulse, all the spins are pointed in a common direction perpendicular to the static field, and they all precess at the Larmor frequency. The net precessing magnetization decays with a time constant T2 because the individual spins rotate at different rates and lose their common phase. At the molecular level, dephasing is caused by random motions of the spins. The magnetic fields of neighboring spins and nearby paramagnetic centers appear as randomly fluctuating magnetic fields to the spins in random motion. In an inhomogeneous field, spins at different locations precess at different rates. Therefore, in addition to the molecular spin-spin relaxation of fluids, spatial inhomogeneities of the applied field also cause dephasing. Spatial inhomogeneities in the field can be due to microscopic inhomogeneities in the magnetic susceptibility of rock grains or due to the macroscopic features of the magnet.

A widely used technique for acquiring NMR data both in the laboratory and in well logging, uses an RF pulse sequence known as the CPMG (Carr-Purcell-Meiboom-Gill) sequence. As is well known, after a wait time that precedes each pulse sequence, a ninety degree pulse causes the spins to start precessing. Then a one hundred eighty degree pulse is applied to keep the spins in the measurement plane, but to cause the spins which are dephasing in the transverse plane to reverse direction and to refocus. By repeatedly reversing the spins using one hundred eighty degree pulses, a series of "spin echoes" appear, and the train of echoes is measured and processed.

Further background, set forth in the referenced copending parent application Ser. No. 08/936,892, is summarized as follows: The static field may be naturally generated, as is the case for the earth's magnetic field $B_E$. The NML™ nuclear logging tool of Schlumberger measures the free precession of proton nuclear magnetic moments in the earth's magnetic field. See, for example, U.S. Pat. No. 4,035,718. The tool has at least one multi-turn coil wound on a core of non-magnetic material. The coil is coupled to the electronic circuitry of the tool and cooperatively arranged for periodically applying a strong DC polarizing magnetic field, $B_p$, to the formation in order to align proton spins approximately perpendicular to the earth's field, $B_E$. The characteristic time constant for the exponential buildup of this spin polarization is the spin-lattice relaxation time, $T_1$. At the end of polarization, the field is rapidly terminated. Since the spins are unable to follow this sudden change, they are left aligned perpendicular to $B_E$ and therefore precess about the earth's field at the Larmor frequency $f_L = \gamma B_E$. The Larmor frequency in the earth's field varies from approximately 1300 to 2600 Hz, depending on location. The spin precession induces in the coil a sinusoidal signal of frequency $f_L$ whose amplitude is proportional to the number of protons present in the formation. The tool determines the volume of free fluid in the formation. Additives in the borehole fluid are required to prevent the borehole fluid signal from dominating the formation signal. Also, there is necessarily a significant wait time before transients die down so that the coil can be used for detecting relatively small magnetic resonance signals.

A further nuclear magnetic resonance approach employs a locally generated static magnetic field, $B_o$, which may be produced by one or more permanent magnets, and RF antennas to excite and detect nuclear magnetic resonance (using, for example, the type of RF pulse sequence first described above), to determine porosity, free fluid ratio, and permeability of a formation. See, for example, U.S. Pat. Nos. 4,717,878 and 5,055,787.

As pointed out in the referenced copending Application, the tools and techniques developed in the prior art have various drawbacks that limit their utility in practical applications. These limitations include, among others, one or more of the following: a shallow depth of investigation, restrictions on the shape and size of the region of investigation, the need for treating of the borehole fluid, and the need for significant waiting between transmission and receiving.

It is among the objects of the present invention to address limitations of prior art nuclear magnetic resonance logging techniques and apparatus, and to devise improved logging methods and equipment for obtaining magnetic resonance characteristics of earth formations surrounding a borehole.

SUMMARY OF THE INVENTION

In the referenced copending U.S. patent application Ser. No. 08/936,892 there is disclosed an apparatus and technique for NMR logging that is based on non-resonant excitation and refocusing and exhibits a number of advantageous features: The volume of investigation is large compared with the conventional resonant operation. Also, the signal coming from different depths can be differentiated by its Larmor frequency. The technique thereof utilizes a pair of magnetic field generating sources, preferable orthogonally wound coils, that can be energized with large currents in a controlled manner to produce orthogonal magnetic fields in the formation. With appropriate switching of the currents, the direction of the generated magnetic field in the formation can then be changed abruptly. The rate of change of the direction of the magnetic field in the formation has to be fast compared to the local Larmor frequency. This way, the spins cannot follow the direction of the magnetic field and the spins end up orthogonal to the applied magnetic field. Effectively, it is as though all the spins have undergone a 90° pulse. (In the conventional resonant excitation, only spins where the applied field is within a particular small range are excited. In practise, this leads to relatively thin shells of sensitive regions.) Now, the spins undergo a free induction decay with a Larmor frequency proportional to the local field produced by the presently activated coil. Since the field produced by the coil in the formation is highly non-uniform, there is a large range of Larmor frequencies and the net magnetization will decay very quickly (that is, $T^*_2$ is very short). This dephasing can be reversed by forming an echo which is achieved by reversing the field abruptly after a time t. The sense of rotation for the precessing spins is reversed and an echo is formed at a total time 2t, when the magnetization of all the spins is in phase again. This can then be repeated over and over to obtain a train of so-called gradient echoes.

Embodiments of the present invention also employ, inter alia, orthogonally oriented coils for transmission and detection, respectively, but do not use the just described technique of forming gradient echoes; instead using earth's magnetic field as the operative static field. As in the above-summarized NML™ tool, summarized in the Background portion hereof, a coil is used to apply a strong magnetic field, with a component perpendicular to earth's magnetic field, that polarizes the spins, and when the applied field is turned off the spins precess around the earth's magnetic field. In a form of the present invention, however, the same coil is not utilized for detecting the spins. Instead, the orthogonally oriented coil is utilized for detection. In an embodiment of this form of the invention, a third coil, preferably having its axis aligned with the tool axis, is used to create a magnetic field primarily in the borehole so that the spins therein precess at a frequency different from the frequency to which the detection system is tuned (namely, the Larmor frequency relatively deep in the formation). There is no need to chemically treat the borehole fluid. Also, in an embodiment of this form of the invention, a technique is used to reduce or eliminate spurious signals in the receiver coil caused by mutual inductance with the transmitting coil during its ring down. In this manner, detection can begin almost immediately after termination of the polarizing field, thereby increasing the sensitivity to spins with short relaxation times.

In accordance with an embodiment of the apparatus of the invention, equipment is provided for determining a nuclear magnetic resonance characteristic of formations surrounding an earth borehole. A logging device is movable through the borehole, the logging device having a longitudinal axis. A magnetic field generating means in the logging device is provided for generating a magnetic field in the formations. A magnetic field detecting means in the logging device is provided for detecting magnetic resonance signals from the formations, the magnetic field detecting means being separate from the magnetic field generating means. Means are provided for applying a polarizing signal to the magnetic field generating means. The magnetic field detecting means is operative, after the polarizing signal, to detect magnetic resonance of spins in the formations that are precessing around earth's magnetic field.

In an embodiment of the apparatus of the invention, there is provided in the logging device a further magnetic field generating means, the further magnetic field generating means being operative to produce a further magnetic field in the borehole that reduces the contribution of spins in the borehole to the magnetic resonance detected by the magnetic field detecting means. In a form of this embodiment, the magnetic field generating means comprises a first coil and means for applying an energizing signal to said first coil, the magnetic field detecting means comprises a second coil that is oriented perpendicular to first coil, and the further magnetic field generating means comprises a third coil.

In accordance with another form of the invention, there is provided a method for measuring a nuclear magnetic resonance characteristic of earth formations surrounding a borehole, comprising the following steps: providing a logging device that is moveable through the borehole; producing, from the logging device, an audio frequency magnetic field in formations surrounding the borehole; reversing the phase of the audio frequency magnetic field in the formations; and detecting, at the logging device, a spin echo from the formations. In the preferred embodiment of this form of the invention, the reversing and detecting steps are repeated a number of times to detect a number of spin echoes from said formations, the reversals of phase being implemented at times τ, 3τ, 5τ . . . , and the spin echoes being detected at times 2τ, 4τ, 6τ . . . .

In accordance with another form of the invention, there is provided a method for determining a nuclear magnetic resonance characteristic of formations surrounding a borehole, comprising the following steps: (a) providing a logging device that is movable through the borehole; (b) producing, from the logging device, a magnetic pulse of a particular duration; (c) detecting, at the logging device, nuclear magnetic resonance signals resulting from the magnetic pulse of step (b); and, (d) repeating steps (b) and (c) for a number of further pulses having respectively different durations. In an embodiment of this form of the invention the magnetic pulses are pulses of audio frequency oscillations that are operative to tip spins in the formations that were initially aligned with earth's magnetic field. In other embodiments, the pulses are adiabatic pulses ro composite pulses.

Further features and advantages of the invention will become more readily apparent from the following detailed description when taken in conjunction with the accompanying drawings.

DETAILED DESCRIPTION

Figure 1:
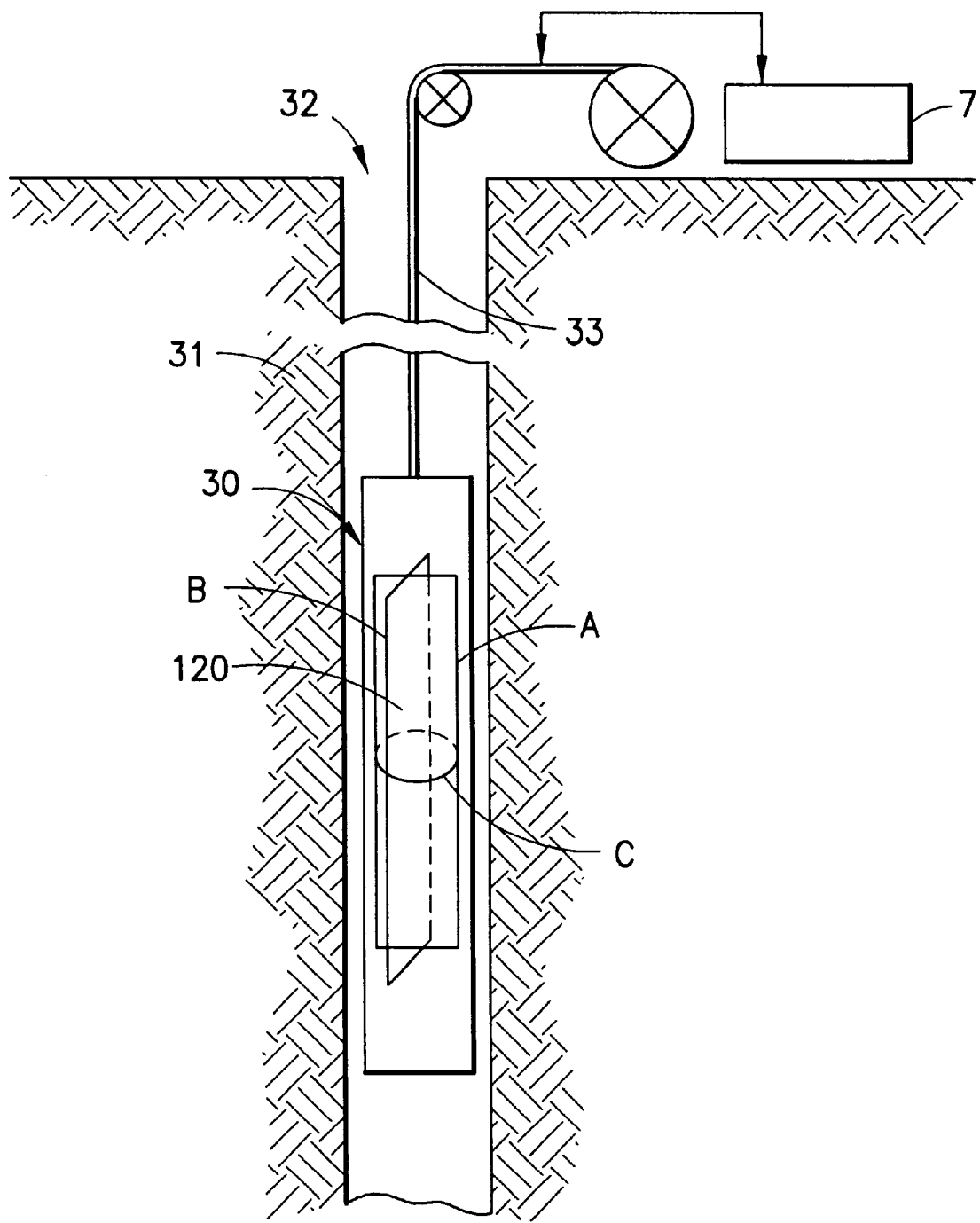
FIG. 1 is a diagram, partially in schematic and partially in block form, that can be used in practicing embodiments of the invention.

Referring to FIG. 1, there is shown an apparatus for investigating subsurface formations 31 traversed by a borehole 32, which can be used in practicing embodiments of the present invention. An investigating apparatus or logging device 30 is suspended in the borehole 32 on an armored cable 33, the length of which substantially determines the relative depth of the device 30. The cable length is controlled by suitable means at the surface such as a drum and winch mechanism. Surface equipment, represented at 7, can be of conventional type, and can include a processor subsystem, communicates with the downhole equipment. Although the logging device or tool 30 is shown as a single body, it may alternatively comprise separate components, and the tool may be combinable with other logging tools. Also, while a wireline is illustrated, alternative forms of physical support and communicating link can be used, for example in a measurement while drilling system.

The tool 30 has a pair of coils, respectively designated as coil A and coil B, wound on a non-conductive core 120, which may be, for example, a non-conductive, magnetically permeable core made of a suitable material such as ferrite, laminated permealloy, or tape-wound metglass. A non-conductive, non-magnetically permeable core could also be used. In the embodiment of FIG. 1, the axis of the logging tool (and the core 120) is a longitudinal axis. The coils A and B are wound on axes that are mutually orthogonal, and are both orthogonal to the longitudinal axis. The coils A and B are preferably elongated in the axial direction, with the elongated legs of the conductor loops thereof being parallel to the longitudinal axis of the tool. The angular density of the windings is preferably sinusoidal to insure a two-dimensional dipolar field distribution. The coils A and B are azimuthally offset by 90° to obtain dipolar field characteristics for the coils A and B that are orthogonal in the formation and to minimize mutual inductance of the coils A, B. The coils can be protected by a nonconductive, nonmagnetic, abrasion and impact resistant cover made of a suitable material such as fiberglass, plastic, ceramic, or a composite of these materials. A further coil, designated coil C, is wound around the longitudinal axis of the core 120. Thus, all three coils are mutually orthogonal.

Figure 2:
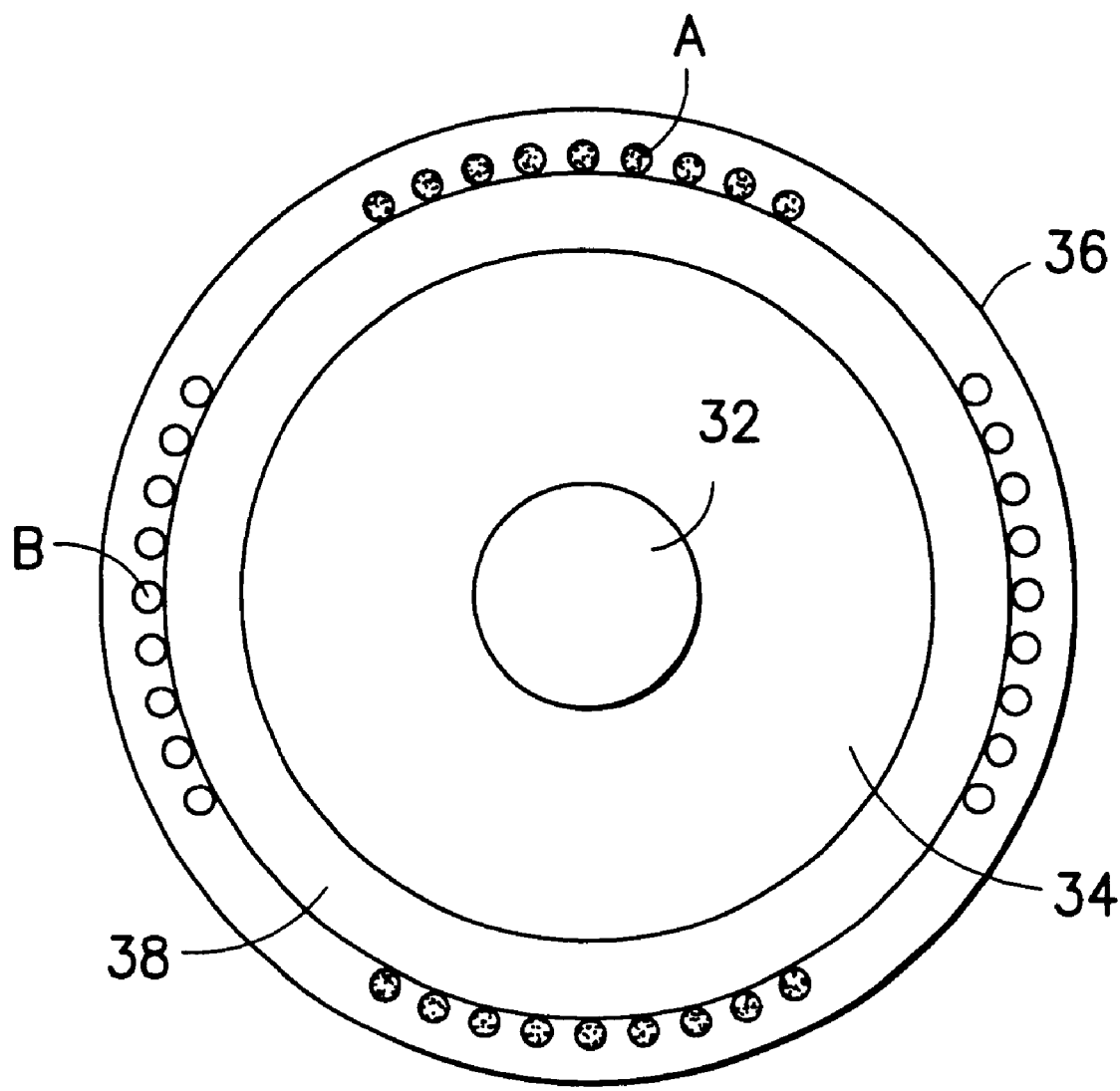
FIG. 2 is a diagram of a cross-section of an embodiment of a logging device for logging while drilling that can be used in practicing embodiments of the invention.

The logging apparatus hereof can be utilized in a logging-while drilling application. FIG. 2 illustrates a cross section of an NMR logging device 30 in the form of a logging-while-drilling tool. The tool 30 includes a mud channel 32 for carrying the borehole fluid through the drill string and a drill collar 34 which has a reduced outer diameter at the section shown. The orthogonal coils A and B are wound on a magnetically permeable, laminated core 38 made of a suitable material such as ferrite, laminated permealloy, or tape wound metglass. The protective cover is shown at 36.

Figure 3:
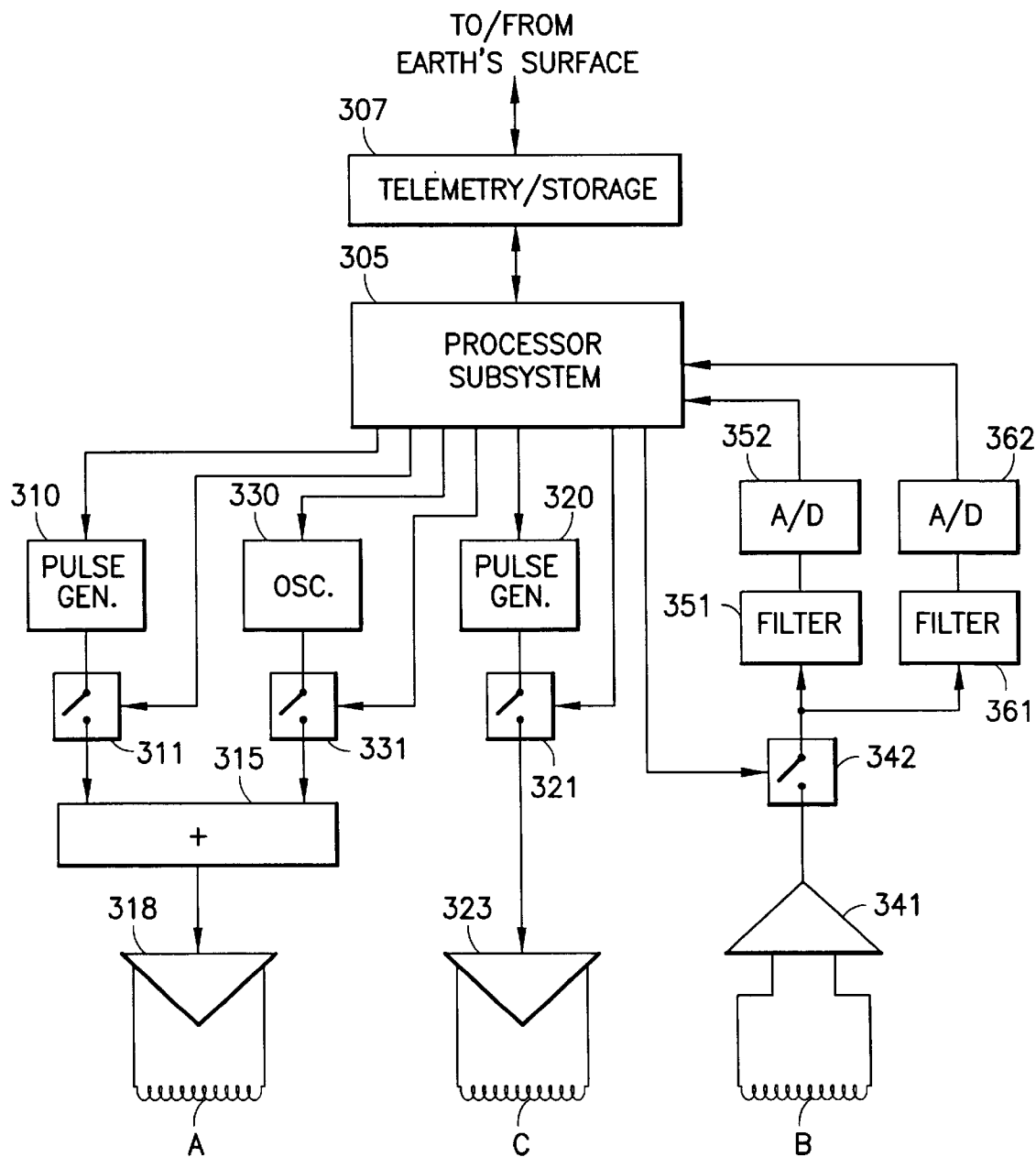
FIG. 3 is a block diagram of downhole circuitry that can be used in practicing embodiments of the present invention.

FIG. 3 is a diagram of downhole electronics that can be utilized in practicing an embodiment of the invention. A downhole processor subsystem is represented at 305. The processor subsystem 305 has associated memory, timing interfaces, and peripherals (not separately shown), as is well known in the art. The processor subsystem is conventionally coupled with telemetry circuitry 307, for communication with the earth's surface. Pulse generators 310, 320, and oscillator 330 are provided. The pulse generator 310 produces the polarizing pulse that is applied to the coil A via electronic switch 311, summing circuit 315, and driving amplifier 318. The pulse generator 320, whose output is coupled to coil C via electronic switch 321 and driving amplifier 323, generates the signal that is used to produce the magnetic field primarily in the borehole that changes the characteristic Larmor frequency of spins in the borehole to be outside the frequency range to which the detector is tuned for detecting spins from the formations. The oscillator 330, whose output is coupled to the coil A via electronic switch 331, summing circuit 315, and driving amplifier 318, is operative to apply the test signal, at a frequency which is outside the range of operating frequencies of the detector circuitry. In accordance with a feature of an embodiment of the invention, the mutual inductance between the coils A and B is determined, and an appropriate correction is applied to minimize spurious signals caused by mutual inductance when the polarizing signal applied to coil A is abruptly turned off and coil B is utilized immediately thereafter for detection. In this manner, the effect of signals induced in coil B during any ring down of coil A (which can also be minimized using appropriate damping circuitry and/or Q-switching circuitry in conjunction with coil A), is minimized. The receiver coil B is coupled, via preamplifier 341 and electronic switch 342, to bandpass filters 351 and 361, respectively, the outputs of which are coupled, via analog-to-digital converters 352 and 362, respectively, to the processor subsystem 305. The filter 351 is for the signal over the primary operating bandwidth, and the filter 361 is for the test signal frequency. Control signals from the processor subsystem 305 can be used to control the electronic switches 311, 321, 331, and 342.

Earth's magnetic field, $B_e$, although relatively weak (0.2 to 0.7 Gauss), is very uniform and everywhere present. In the embodiment being described, assume that $B_e$ has a dominant component generally in the direction of the borehole axis (and the tool axis). [The converse case can be handled by changing the roles of the coils.] The coil C is energized to produce a magnetic dipole moment parallel to the borehole axis, and thus a field $B_z$ parallel to the dominant component of $B_e$ and which falls off rapidly. This will alter the local Larmor frequency in the borehole and make the spins in the borehole process at a frequency that is different than the frequency the detection system is tuned to; that is, in embodiments hereof, the Larmor frequency deep in the formation. The magnitude of $B_z$ in the borehole, in the region of the logging tool, can be rather small; for example of the order of $B_e$. Accordingly, the mud in the borehole need not be doped. Now, the coil A can be used to produce a field $B_A$ in a direction orthogonal to $B_e$ to tip the spins in the formations into the plane perpendicular to the direction of earth's magnetic field. This can be implemented under control of the processor subsystem 305 which enables the pulse generator 310 and electronic switch 311 to produce the polarizing signal. The strong static current used to polarize the spins causes the formation to acquire a magnetization≈$\chi B_A/\mu_0$, where $\chi$ is the susceptibility of the spins and $\mu_0$ is the magnetic permeability of free space. The polarizing current will preferably be applied for at least several seconds. The polarizing signal is then shut off. Now, with the spins precessing around earth's magnetic field, the transient signals are acquired. In the present embodiment, the coil B, which is orthogonal to coils A and C, is used as a receiver coil to pick up the signals from the spins precessing around the earth's magnetic field. In accordance with a feature of the present embodiment, the effect of mutual coupling between coil A and coil B is reduced using a lock-in technique which employs currents at frequencies much different from the Larmor frequency in the formations. The equation of motions for spins during transients can be solved (see, for example, Melton and Pollack, JMRA 122, p 42–49, 1996) and the corresponding induced voltage can be computed. The effect of spin relaxation on spin dynamics can be calculated. From the transient signal one can deduce the time dependent magnetization and hence the relaxation times. In other words, the transient signal contains the information on the spin dynamics of the system.

Figure 4:
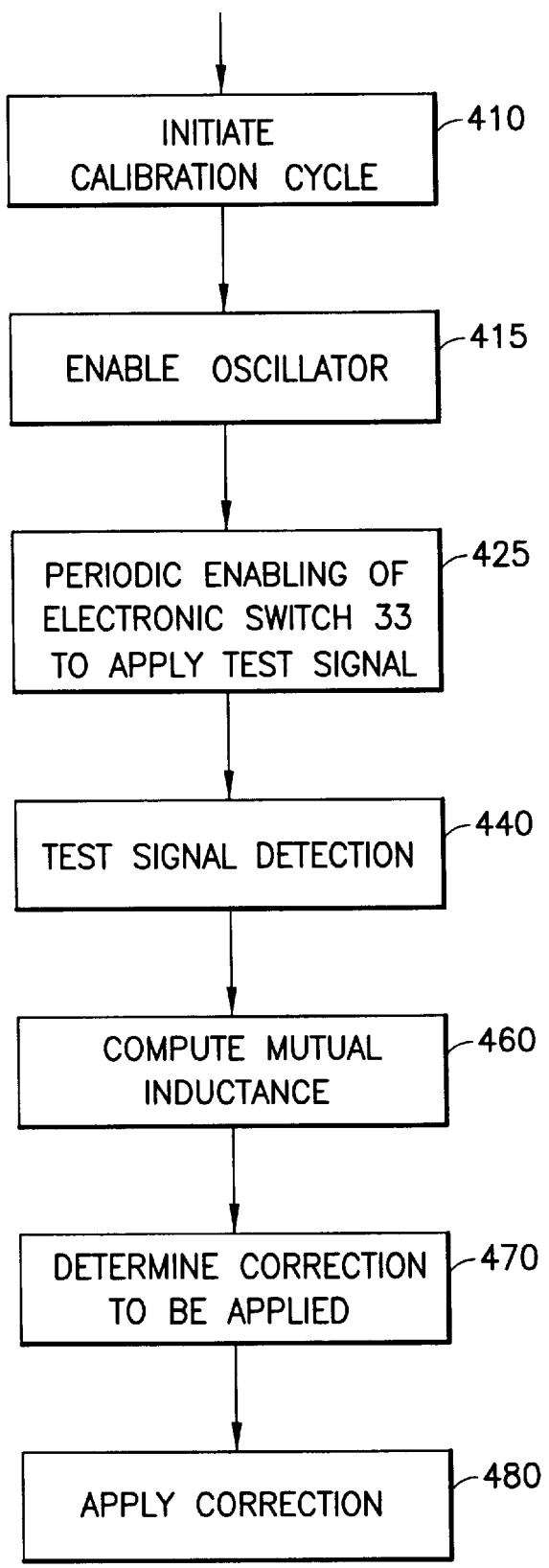
FIG. 4 is a flow diagram of a routine that can be utilized to control the processor subsystem of the FIG. 3 embodiment in practicing a feature in accordance with the invention.

Referring to FIG. 4, there is shown a flow diagram of a routine for controlling a processor, for example the downhole processor subsystem 305 (and/or such processor under control from uphole), to implement the correction for spurious signals in coil B caused by mutual inductance with coil A during its transient stage after shut off. The block 410 represents initiation of the calibration cycle which, in the present embodiment, is performed periodically (for example every 100 milliseconds), with a cycle time that can be predetermined or, for example, controlled from uphole. In the present embodiment, it is not necessary to interrupt operation of the primary measurement system to perform the calibration cycle, although it will be understood that operation of the calibration cycle could also be implemented when the primary system is not operative in a detection mode. The blocks 415 and 425 respectively represent the enabling of oscillator 330, and the periodic control of electronic switch 331, so that the test signal is periodically applied to the coil A. The block 440 represents the coordinated periodic detection of the test signal received via coil B and the branch through bandpass filter 361. The block 460 represents computation of the mutual inductance, the block 470 represents the determination of the correction to be applied, and the block 480 represents application of the appropriate correction signal, which can be implemented, for example, in software form.

Figure 5:
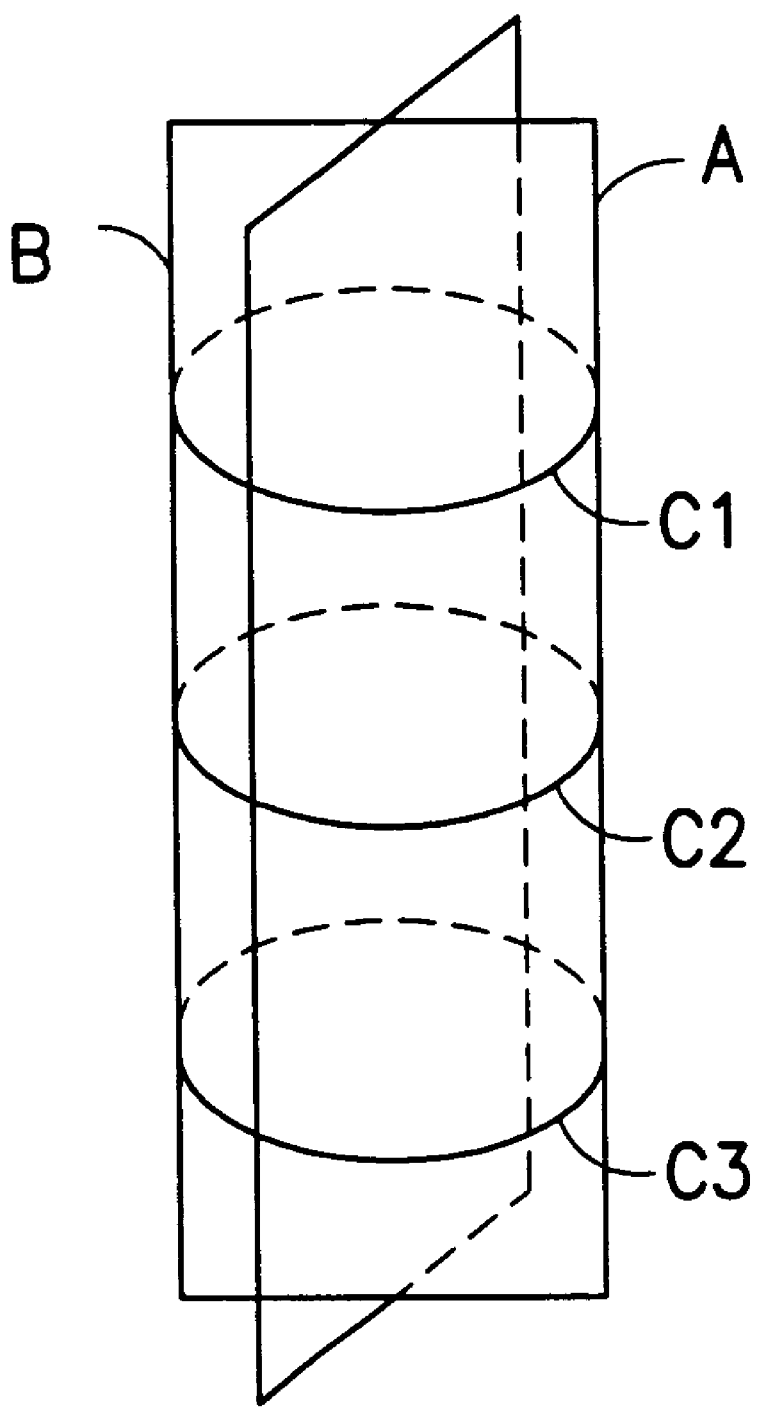
FIG. 5 is a diagram illustrating a further embodiment of the invention that utilizes a plurality of axially wound coils to obtain a desired magnetic field pattern in the borehole.

FIG. 5 illustrates a variation of the FIG. 1 embodiment wherein a plurality of axially wound coils are utilized in producing a magnetic field in the borehole, in the region of the logging tool, that is effective in reducing or eliminating the signal from the borehole at a frequency related to the characteristic Larmor frequency of earth's magnetic field. A plurality of coils (three coils, C1, C2 and C3 being illustrated in this example) can more precisely shape the magnetic field in the borehole and reduce the magnetic field in the formations that might affect the measurements.

A further form of the invention employs a rotary spin echo technique (see Solomon, Phys. Rev. Lett. 2, 301,1952). In an embodiment of this form of the invention, earth's magnetic field is again utilized. In this embodiment, a tipping signal is applied, for a time $\tau$, to coil A at the Larmor frequency of earth's magnetic field. Since the Larmor frequency of the geomagnetic field is in the range between about 1 kHz and 3 kHz, the applied signal is an audio frequency (AF) signal that is operative to tip spins in the formation. In FIG. 3, the pulse generator 310 would be modified to include an audio frequency oscillator. After the time $\tau$, the phase of the AF signal is reversed (e.g. by gating in a phase shifted version of the AF oscillator signal in equipment of the type shown in FIG. 3), and this signal is applied for a time $\tau$ as the spins return to their originally polarized direction (that is, to be aligned again with the geomagnetic field), whereupon a spin echo is sensed by coil B. As above the coil or coils C can be used to eliminate the borehole signal, and mutual coupling between coils A and B can be reduced using the previously described technique.

As compared to approaches that employ a polarizing current, there is no concomitant loss due to switching off of the polarizing current. The magnetization of earth's field is uniform, as compared to the typical $1/r^2$ fall off for a coil generated field. Upon phase shift, the magnetization vector at each point precesses at the same rate as before the phase shift out in the opposite direction, and the angle of precession will cancel and all the spins will be in phase along the z'-axis (of the rotating frame) producing an echo. The receiving coil is tuned to the "absorption" mode so that the signal detected is directly proportional to $M_{y'}$. The oscillatory signal has a maximum when the magnetization is along y' (which is normal to z') at the actual echo. This, however does not affect the decay rate of the maxima. By varying $\tau$, the effective relaxation can be measured as $1/T_{\rho}=(\frac{1}{2})*(1/T_1+1/T_2)$. This relaxation time $T_{\rho}$ will depend on the pores-size distribution, bound-fluid relaxation time and other petrophysical properties, just as the currently measured $T_2$ does. Having a slower decay due to $T_1$ can be advantageous when $T_2$ is short compared to $T_1$. Several echoes are obtained by implementing 180° phase shift at times $t=\tau, 3\tau, 5\tau, \ldots$ and observing the echoes at times $t=2\tau, 4\tau, 6\tau \ldots$ A remarkable feature of rotary echoes is that phase errors are not cumulative (similar to CPMG). As the geomagnetic field is remarkably homogeneous, the so called $B_0$ inhomogeneities will be minimal; i.e., the deviations from y'z' plane, due to fluctuation in the local field $\omega_0$, will be minimal.

A related approach can be implemented by modifying existing types of NMR apparatus and techniques that utilize a polarizing static magnetic field $B_0$, for example the types of logging apparatus that are disclosed in U.S. Pat. No. 5,055,788 or U.S. Pat. No. 4,710,713, each of which employs one or more permanent magnets to generate $B_0$. In the existing apparatus, the inhomogeneities in $B_0$ and $B_1$ are overcome, to a large extent, by CPMG techniques. In the rotating frame the inhomogeneities are made small by requiring that the rf field is large so that $\omega_1 >> |\omega_0-\omega|$. In this case, both $B_0$ and $\omega_1 >> |\omega_0-\omega|$ are in a plane perpendicular to the borehole axis; hence, pick-up coils can be used which are axially wound so that pick up is along the bore-hole axis (like the coils $C_1$, $C_2$, and $C_3$ of FIG. 5, but in a receiving mode). With $\omega_1 >> |\omega_0-\omega|$ in each volume element of the sample, the effective frequency $\omega_{\text{eff}}=[(\omega_0-\omega)^2+\omega_1^2]^{(1/2)} \cong \omega_1$. This makes the rotation angle independent of the inhomogeneity of the dc field $\omega_0$ over the volume where the inequality $\omega_1 >> |\omega_0-\omega|$ holds and the rotary spin-echo scheme (as above) then takes care of the variability in $\omega_1$.

In a further variation, instead of a 180° phase shift at time $\tau$, the DC field is increased by an amount $b_0 >> B_1$ for a time period $\tau$ after which $b_0$ is turned off. This can be achieved by coils which produce magnetic field perpendicular to the borehole wall. With $b_0$ on, the effective field lies along z and the time period $\tau$ is chosen such that spins flip around z' by 180°. Then the spins precess back, around x', to form an echo. [See E. J. Wells And K. H. Abramson, JMR, 1, 378 (1969).]

For the case of inhomogeneous rf and offsets, the desired rotation of spins is often not possible by simply turning on the fields for a fixed duration. Adiabatic and composite pulses can be used. Composite pulses are made up of a sequence of rotations of various angles around various axes to obtain, at the end of the sequence, the desired rotation. In adiabatic pulses, both the amplitude and the phase of the applied field are varied as a function of time. The rate of change of the direction of the total magnetic field is slow compared to the instantaneous Larmor frequency. This way, the spins are made to follow the applied magnetic field which is controlled by the currents in the coil. Recently, extremely fast (60 micro second) adiabatic pulses have been devised which are insensitive to a wide range of off-set and rf strength variations (several kHZ). [See Hwang VanZijil and Garwood, JMR, 133, 200 (1998)].

In the above-referenced NML technique, only FID was used. However with $B_1$-insensitive fast adiabatic pulses (as in Ugurbill and Garwood, supra), it is possible to rotate the spins either in a slice or over the entire formation around an axis. This way, echoes can be formed which allow improved signal to noise ratio and formation evaluation.

Figure 6:
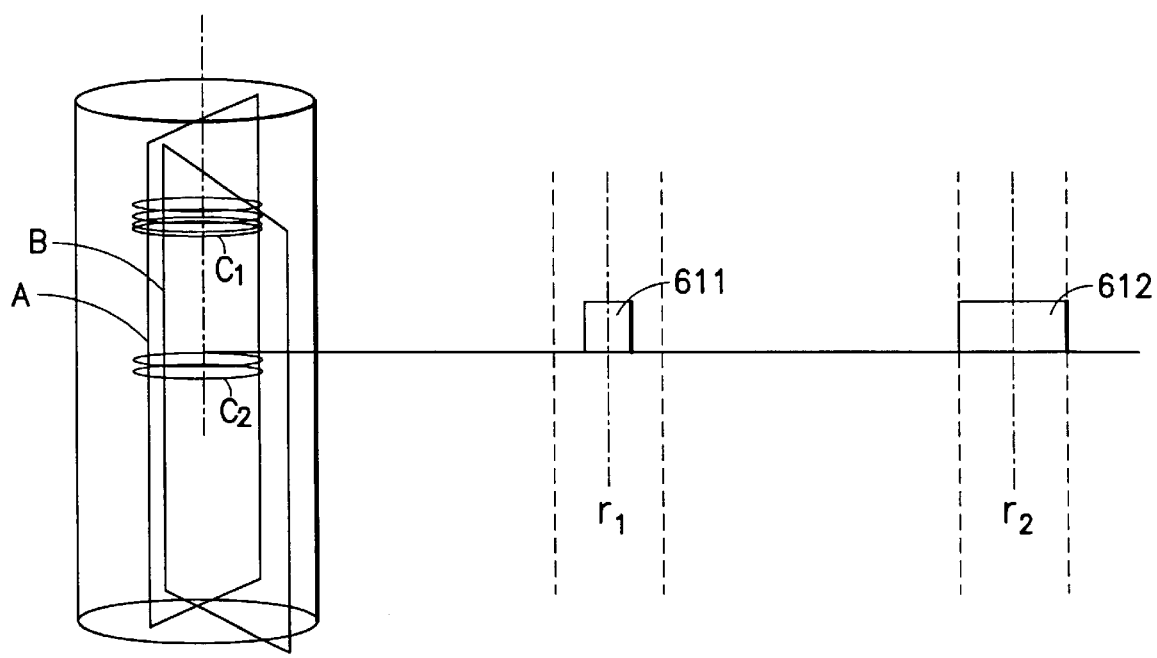
FIG. 6 is a diagram illustrating operation of a further form of the invention.

A further form of the invention utilizes a technique that takes advantage of the fact that as the field strength from the coil (e.g. the coil used to generate an audio frequency (AF) magnetic field at the Larmor frequency of the geomagnetic field) falls off with radial distance (r) from the borehole, it takes a longer pulse (of such AF) to tip the spins by a given amount (e.g., into a transverse plane). [Reference can be made to existing techniques used for locating subsurface water with surface equipment and in which pulse durations are modified.] In an embodiment of this form of the invention, the coil A (FIG. 1) is utilized to produce pulses of audio frequency electromagnetic energy which will operate on spins in the formation that are initially aligned with the geomagnetic field, and the tipping angle will be proportional to the product of the magnetic field strength and the pulse duration. Accordingly, for a particular pulse duration (and since the magnetic field strength will fall off with r) there will be a radial range over which the spins will be tipped to or near the transverse plane, and the signal from this generally annular region of formation (e.g. the FID signal therefrom) can be detected using coil B. To obtain the same degree of tipping at a further radial distance, a longer pulse duration can be used. This is illustrated, for example, in FIG. 6 which shows an approximate region (in dashed line) centered at a radial distance $r_1$ that will be tipped into the transverse plane by a pulse 611 of given duration, and the same at a radial distance $r_2$ for a pulse 612 of longer duration. Thus, by utilizing a series of pulses of different durations and detecting NMR signals from each, a region selective or "slice selective" set of measurements is achieved. The resultant signals can be used to obtain an NMR image of the formations. A further technique is to apply adiabatic pulses which are slice-selective (see Ugurbill and Garwood, in "NMR basic principles and progress", M. Ruin and J. Seelig, Eds., p 109, Springer-Verlag, N.Y., 1992).

As first noted above, in situations where the dominant component of earth's magnetic field is not in the longitudinal borehole direction (that is, along the tool axis), the coil functions can be switched to use, as the polarizing coil, the axially wound coils (or coils) which, in such case, will produce magnetic field components in an investigative region of the formations that are perpendicular to the dominant component of earth's magnetic field. Switching of the coil functions can be implemented by a switching circuit under control of the processor subsystem. Information regarding the direction of earth's magnetic field, with respect to the tool direction, can be obtained, for example, from a direction and inclination tool. This information can be used by an operator uphole to implement the switching or, if desired, it can be implemented automatically.

What is claimed is:

1. Apparatus for determining a nuclear magnetic resonance characteristic of earth formations surrounding a borehole, comprising:
   a logging device movable through the borehole, said logging device having a longitudinal axis;
   magnetic field generating means, in said logging device, for generating a magnetic field in the formations;
   magnetic field detecting means, in said logging device, for detecting magnetic resonance signals from the formations, said magnetic field detecting means being separate from said magnetic field generating means;
   means for applying a polarizing signal to said magnetic field generating means;
   said magnetic field detecting means being operative, after said polarizing signal, to detect magnetic resonance of spins in the formations that are precessing around earth's magnetic field; and
   further magnetic field generating means in said logging device, said further magnetic field generating means being operative to produce a further magnetic field in the borehole that reduces the contribution of spins in the borehole to the magnetic resonance detected by said magnetic field detecting means.

2. Apparatus as defined by claim 1, wherein said magnetic field generating means comprises a first coil and means for applying an energizing signal to said first coil.

3. Apparatus as defined by claim 2, wherein said magnetic field detecting means comprises a second coil.

4. Apparatus as defined by claim 3, wherein said magnetic field detecting means comprises a second coil having a second axis that is substantially perpendicular to said longitudinal axis and substantially perpendicular to said first axis.

5. Apparatus as defined by claim 4 wherein said further magnetic field generating means comprises a third coil having an axis corresponding with said longitudinal axis.

6. Apparatus as defined by claim 4, wherein said further magnetic field generating means comprises a plurality of spaced apart third coils, each having an axis corresponding with said longitudinal axis.

7. Apparatus as defined by claim 3, wherein said further magnetic field generating means comprises a third coil.

8. Apparatus as defined by claim 1, wherein said logging device has a longitudinal axis, and wherein said magnetic field generating means comprises a first coil having a first axis that is substantially perpendicular to the longitudinal axis of said logging device.

9. Apparatus as defined by claim 8, wherein said magnetic field detecting means comprises a second coil having a second axis that is substantially perpendicular to said longitudinal axis and substantially perpendicular to said first axis.

10. Apparatus as defined by claim 9, further comprising circuit means coupled with said second coil for reducing spurious signals in said second coil which are inductively coupled from said second coil to said first coil.

11. Apparatus as defined by claim 10, wherein said circuit means coupled with said second coil includes means operative to determine mutual inductance between said first and second coils.

12. Apparatus as defined by claim 11, wherein said circuit means coupled with said second coil includes means for dynamically measuring said mutual inductance.

13. Apparatus as defined by claim 12, wherein said means for dynamically measuring said mutual inductance includes means for periodically applying a test signal to said first coil, and means for detecting the test signal in said second coil, the detected test signal being indicative of said mutual inductance.

14. Apparatus as defined by claim 13, wherein said circuit means coupled with said second coil is operative to apply said test signal to said first coil during the same time that an energizing signal is applied to said first coil to produce said magnetic field in the formations.

15. Apparatus as defined by claim 14, wherein said magnetic field detecting means includes detection circuitry coupled with said second coil, said detection circuitry being operative to detect the magnetic resonance of said spins over a particular range of frequencies, and said test signal has a frequency that is outside said range of frequencies of said energizing signal.

16. A method for the determining a nuclear magnetic resonance characteristic of earth formations surrounding a borehole, comprising the steps of:

providing a logging device that is movable through the borehole, said logging device having a longitudinal axis;

providing a first coil, in said logging device, for generating a magnetic field in the formations;

providing a second coil in said logging device;

applying a polarizing signal to said first coil;

detecting, with said second coil, magnetic resonance of spins in the formations that are precessing around earth's magnetic field; and providing a third coil in said logging device, said third coil being operative to produce a further magnetic field in the borehole that reduces the contribution of spins in the borehole to the magnetic resonance detected by said second coil.

17. The method as defined by claim 16, further comprising the step of reducing spurious signals in said second coil which are inductively coupled from said second coil to said first coil.

18. The method as defined by claim 17, wherein said step of reducing spurious signals in said second coil includes determining the mutual inductance between said first and second coils.

19. The method as defined by claim 18, wherein the determining of mutual inductance includes the steps of periodically applying a test signal to said first coil, and detecting the test signal in said second coil, the detected test signal being indicative of said mutual inductance.

20. The method as defined by claim 19, further comprising applying said test signal to said first coil during the same time that an energizing signal is applied to said first coil to produce said magnetic field in the formations.

21. A method for the determining a nuclear magnetic resonance characteristic of earth formations surrounding a borehole, comprising the steps of:

providing a logging device that is movable through the borehole, said logging device having a longitudinal axis;

providing a first coil, in said logging device, for generating a magnetic field in the formations;

providing a second coil in said logging device;

applying a polarizing signal to said first coil;

detecting, with said second coil, magnetic resonance of spins in the formations that are precessing around earth's magnetic field; and reducing spurious signals in said second coil which are inductively coupled from said second coil to said first coil.

22. The method as defined by claim 21, wherein said step of reducing spurious signals in said second coil includes determining the mutual inductance between said first and second coils.

23. The method as defined by claim 22, wherein the determining of mutual inductance includes the steps of periodically applying a test signal to said first coil, and detecting the test signal in said second coil, the detected test signal being indicative of said mutual inductance.

24. The method as defined by claim 23, further comprising applying said test signal to said first coil during the same time that an energizing signal is applied to said first coil to produce said magnetic field in the formations.

* * * * *